United States Patent
Haraya et al.

(10) Patent No.: US 10,117,820 B2
(45) Date of Patent: Nov. 6, 2018

(54) COSMETIC COMPOSITION

(71) Applicant: AJINOMOTO CO., INC., Chuo-ku (JP)

(72) Inventors: Nana Haraya, Kawasaki (JP); Takanori Sugimoto, Yokkaichi (JP); Takuya Okada, Chuo-ku (JP)

(73) Assignee: AJINOMOTO CO., INC., Chuo-ku (JP)

( * ) Notice: Subject to any disclaimer, the term of this patent is extended or adjusted under 35 U.S.C. 154(b) by 0 days.

(21) Appl. No.: 15/170,072

(22) Filed: Jun. 1, 2016

(65) Prior Publication Data
US 2016/0354294 A1  Dec. 8, 2016

(30) Foreign Application Priority Data
Jun. 2, 2015  (JP) ................ 2015-112637

(51) Int. Cl.
| | | |
|---|---|---|
| *A61K 8/49* | (2006.01) | |
| *A61K 8/35* | (2006.01) | |
| *A61K 8/34* | (2006.01) | |
| *A01N 25/00* | (2006.01) | |
| *A61Q 19/10* | (2006.01) | |
| *A61K 8/40* | (2006.01) | |
| *A61Q 19/00* | (2006.01) | |
| *A61K 8/42* | (2006.01) | |
| *A01N 31/02* | (2006.01) | |
| *A01N 31/08* | (2006.01) | |

(52) U.S. Cl.
CPC ............ *A61K 8/4913* (2013.01); *A01N 25/00* (2013.01); *A01N 31/02* (2013.01); *A01N 31/08* (2013.01); *A61K 8/345* (2013.01); *A61K 8/35* (2013.01); *A61K 8/40* (2013.01); *A61K 8/42* (2013.01); *A61Q 19/00* (2013.01); *A61Q 19/10* (2013.01); *A61K 2800/30* (2013.01); *A61K 2800/524* (2013.01)

(58) Field of Classification Search
None
See application file for complete search history.

(56) References Cited

U.S. PATENT DOCUMENTS

| | | |
|---|---|---|
| 2009/0143489 A1 | 6/2009 | Winn |
| 2011/0268676 A1 | 11/2011 | Winn |
| 2012/0214671 A1 | 8/2012 | Parant et al. |
| 2012/0289575 A1 | 11/2012 | Lu et al. |
| 2015/0010489 A1 | 1/2015 | Sugimoto |
| 2015/0111859 A1 | 4/2015 | Sugimoto et al. |
| 2015/0148421 A1 | 5/2015 | Winn |
| 2016/0015031 A1 | 1/2016 | Pesaro et al. |

FOREIGN PATENT DOCUMENTS

| | | | |
|---|---|---|---|
| EP | 2774481 | * | 9/2014 |
| EP | 2 832 345 A1 | | 2/2015 |
| EP | 2 870 958 A1 | | 5/2015 |
| WO | WO 2009/070736 A1 | | 6/2009 |
| WO | WO 2012/004896 A1 | | 1/2012 |
| WO | WO 2013/147328 A1 | | 10/2013 |
| WO | WO 2014/135650 A1 | | 9/2014 |

OTHER PUBLICATIONS

Extended European Search Report dated Oct. 13, 2016 in Patent Application No. 16172597.3.
Partial European Search Report dated Jul. 27, 2016 in Patent Application No. 16172597.3.
Jun Matsuda, "Science and Technology to Ensure the Safety of Cosmetics", CMC books, chapter 9, 2014, pp. 75-89 and Cover Pages.
"Optimal Addition Method of Antiseptics and Preservatives to Food, Cosmetic, Pharmaceutical Product", Technical Information Institute Co., Ltd., 2014, pp. 225-229 and Cover Pages.
Nobukasu Kashima, et al., "Inhibition of Bacteriophages of Amino Acid Producing Bacteria by N-Acylamino Acids", Agricultural and Biological Chemistry, vol. 40, No. 1, XP002759866, 2014, pp. 41-47 and Cover Page.

* cited by examiner

*Primary Examiner* — Bong-Sook Baek
(74) *Attorney, Agent, or Firm* — Oblon, McClelland, Maier & Neustadt, L.L.P.

(57) ABSTRACT

Provided is a cosmetic composition superior in antiseptic property and having high moisturizing property. A cosmetic composition containing (A) particular acylproline or a salt thereof, and (B) particular hydroxamic acid derivative, particular acetophenone derivative or diol compound.

20 Claims, No Drawings

COSMETIC COMPOSITION

TECHNICAL FIELD OF THE INVENTION

The present invention relates to a cosmetic composition having high antimicrobial property and superior in preservative quality, which comprises a particular acylproline, and a particular hydroxamic acid derivative, acetophenone derivative or diol compound. Also, the present invention relates to a method of preserving cosmetics, comprising adding the above.

BACKGROUND OF THE INVENTION

Cosmetics are assumed to be used for a long term, and constantly at a risk of contamination. Therefore, a preservative is indispensible. On the other hand, since the image of preservatives is worsening due to the aspiration to safety in recent years, various preservatives such as paraben and the like are not favored by consumers in the market. Accordingly, a technique for preserving cosmetics without using such preservatives is desired (non-patent document 1).

However, many problems occur in preserving cosmetics without adding a preservative, and many problems were experienced in actual formulation design, such as (i) limitation on pH (need to lower the formulation pH and the like), (ii) limitation on the containers and methods to be used due to an insufficient antiseptic effect, and (iii) an adverse influence on the sense of use by a material added for an antiseptic effect (e.g., to decrease water activity and the like) since it causes sliminess and stickiness (non-patent document 2). In such cases, prevention of mold (fungus) is known to be particularly difficult since it shows a wider water activity permitting growth, and a growth optimal pH on the acidic side (non-patent documents 1, 2).

In addition, since cosmetics are often used around water, which is particularly suitable for the growth of microorganisms, and refillable products are increasingly used backed by the awareness of environmental issues in recent years, the risk of contamination with microorganisms increases due to the reuse of containers. In this situation, the standard shown in, for example, the Pharmacopoeia (the Japanese Pharmacopoeia, supplement of the $14^{th}$ edition, 5. preservatives effectiveness test) may not be sufficient. Generally, it is requested that three kinds of bacteria and *Candida* reach an eradication level of 10 or less viable counts within 7 days from inoculation and do not grow thereafter, and *Aspergillus brasiliensis* show a remarkable decrease in the viable counts at an early stage after inoculation. Particularly, when a container is reused, bacteria that acquired resistance to antibacterial agents may emerge, and the standard for bacteria is set to a higher level than usual, as evidenced by the use of a test method for examining the easiness of developing resistant bacteria and the like.

While a method of preserving cosmetics by using alkylhydroxamic acid and alcohol, particularly diols, has been proposed, this method shows only an insufficient antiseptic effect on *Aspergillus brasiliensis* and the like (patent document 1). Furthermore, since low molecule diols show a high influence on the sense of use and formulation, an increase in the amount of use thereof is not preferable.

Since 4-hydroxyacetophenone has an antiseptic effect, a method of preserving cosmetics by using same in combination with various antiseptic materials has been proposed (patent documents 2, 3). However, application thereof to cosmetics is problematic, since 4-hydroxyacetophenone has a peculiar odor unfavorable for cosmetics, and cannot be added in large amounts to enhance an antiseptic effect and the like.

Furthermore, hexylglycerol is also known to have an antiseptic effect. However, addition thereof in large amounts to cosmetics and the like affects texture and viscosity, and is feared to cause irritation. Therefore, the amount of use thereof is limited. On the other hand, low-irritative cyclohexylglycerol is known to show only a weak antiseptic effect and requires addition in large amounts, thereby causing an influence on the texture and viscosity.

It has been reported that decanoylproline or a salt thereof has a superior moisturizing effect, and can provide cosmetics superior in the sense of use while suppressing the smell of antimicrobial agents having a problematic smell (patent document 4).

DOCUMENT LIST

Patent Documents

[patent document 1] WO 2009-070736
[patent document 2] WO 2014-135650
[patent document 3] JP-A-2014-172908
[patent document 4] WO 2013-147328

Non-Patent Document

[non-patent document 1] Science and Technology to Ensure the Safety of Cosmetics (CMC books), chapter 9
[non-patent document 2] Optimal Addition Method of Antiseptics and Preservatives to Food, Cosmetic, Pharmaceutical Product (Technical Information Institute Co., Ltd.) p225-229

SUMMARY OF THE INVENTION

Problems to be Solved by the Invention

A problem of the present invention is provision of a cosmetic composition superior in an antiseptic effect against bacteria and fungi, particularly mold, over a wide pH range, and not requiring addition of conventional preservatives represented by paraben and the like.

Means of Solving the Problems

The present inventors have conducted intensive studies in an attempt to solve the aforementioned problem and found that an antiseptic effect can be enhanced by combining a particular hydroxamic acid derivative, an acetophenone derivative or a diol compound with acylproline, and that such combination enables provision of cosmetics free of a peculiar odor and superior in the sense of use, moisturizing property and preservative quality, which resulted in the completion of the present invention.

Accordingly, the present invention includes the following embodiments.

[1] A cosmetic composition comprising the following (A) and (B):
(A) an acylproline represented by the formula (I) or a salt thereof;

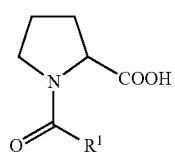

(I)

wherein an acyl group represented by R¹—CO— is an acyl group induced from a saturated or unsaturated fatty acid having 2-23 carbon atoms, (B) at least one kind selected from the group consisting of a compound represented by the formula (II) or a salt thereof;

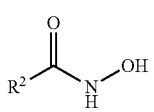

(II)

wherein $R^2$ is an alkyl group having 5-11 carbon atoms, an alkenyl group having 5-11 carbon atoms, an alkynyl group having 5-11 carbon atoms or an alkoxy group having 5-11 carbon atoms, and a compound represented by the formula (III) or a salt thereof;

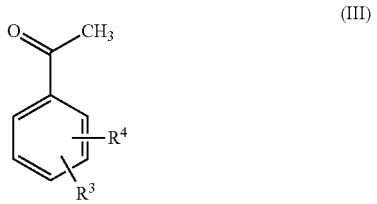

(III)

wherein $R^3$ and $R^4$ are each independently hydrogen, a hydroxy group or —OCH₃.

[2] The composition of [1], wherein (A) an acyl group represented by R¹—CO— is an acyl group induced from a saturated or unsaturated fatty acid having 4-18 carbon atoms.

[3] The composition of [1] or [2], wherein (A) an acylproline represented by the formula (I) is decanoylproline.

[4] The composition of any one of [1]-[3], wherein (B) $R^2$ is an alkyl group having 5-11 carbon atoms.

[5] The composition of any one of [1]-[4], wherein (B) a compound represented by the formula (II) is octanohydroxamic acid.

[6] The composition of any one of [1]-[5], wherein (B) a compound represented by the formula (III) is

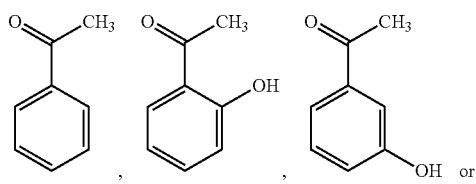

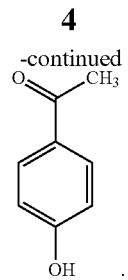

[7] The composition of any one of [1]-[6], further comprising (C) a diol compound having 2-12 carbon atoms.

[8] The composition of [7], wherein (C) a diol compound having 2-12 carbon atoms is one or more compounds selected from the group consisting of a 1,2-diol compound, a 1,3-diol compound and dipropyleneglycol.

[9] The composition of [7] or [8], wherein (C) a diol compound having 2-12 carbon atoms is one or more compounds selected from the group consisting of 1,2-pentanediol, 3-methyl-1,3-butanediol, 1,2-hexanediol, 1,3-butyleneglycol, 1,2-propanediol, 1,3-propanediol, caprylylglycol, glyceryl monocaprate, glyceryl monocaprylate and dipropyleneglycol.

[10] The composition of [7], wherein (C) a diol compound having 2-12 carbon atoms is one or more compounds selected from the group consisting of hexylglycerol and cyclohexylglycerol.

[11] The composition of any one of [1]-[10], wherein the content of (A) in the composition is 0.001-5 wt %.

[12] The composition of any one of [1]-[11], wherein the content of (B) a compound represented by the formula (II) or a salt thereof in the composition is 0.001-1 wt %.

[13] The composition of any one of [1]-[11], wherein the content of (B) a compound represented by the formula (III) or a salt thereof in the composition is 0.005-5 wt %.

[14] The composition of any one of [7]-[13], wherein the content of (C) in the composition is 0.01-15 wt %.

[15] A cosmetic composition comprising the following (A) and (C):

(A) an acylproline represented by the formula (I) or a salt thereof

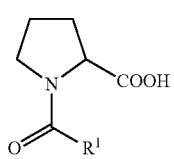

(I)

wherein an acyl group represented by R¹—CO— is an acyl group induced from a saturated or unsaturated fatty acid having 2-23 carbon atoms, (C) a diol compound having 2-12 carbon atoms.

[16] The composition of [15], wherein (C) a diol compound having 2-12 carbon atoms is one or more compounds selected from the group consisting of hexylglycerol and cyclohexylglycerol.

[17] The composition of [16], wherein the content of hexylglycerol or cyclohexylglycerol in the composition is 0.01-4 wt %.

[18] A method of preserving cosmetics, comprising a step of adding the following (A) and (B) to cosmetics:

(A) an acylproline represented by the formula (I) or a salt thereof

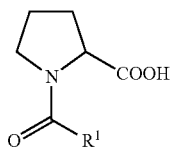

wherein an acyl group represented by $R^1$—CO— is an acyl group induced from a saturated or unsaturated fatty acid having 2-23 carbon atoms,
(B) at least one kind selected from the group consisting of a compound represented by the formula (II) or a salt thereof;

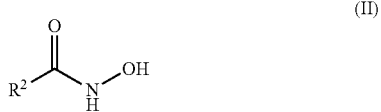

wherein $R^2$ is an alkyl group having 5-11 carbon atoms, an alkenyl group having 5-11 carbon atoms, an alkynyl group having 5-11 carbon atoms or an alkoxy group having 5-11 carbon atoms, and
a compound represented by the formula (III) or a salt thereof;

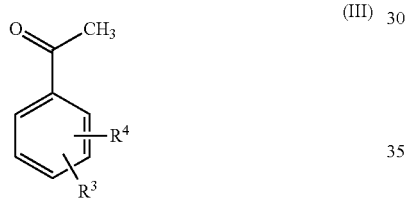

wherein $R^3$ and $R^4$ are each independently hydrogen, a hydroxy group or —OCH$_3$.
[19] The method of [18], further comprising a step of adding (C) a diol compound having 2-12 carbon atoms.
[20] The method of [19], wherein (C) a diol compound having 2-12 carbon atoms is one or more compounds selected from the group consisting of hexylglycerol and cyclohexylglycerol.
[21] A method of preserving cosmetics, comprising a step of adding the following (A) and (C) to cosmetics:
(A) an acylproline represented by the formula (I) or a salt thereof

wherein an acyl group represented by $R^1$—CO— is an acyl group induced from a saturated or unsaturated fatty acid having 2-23 carbon atoms, and
(C) a diol compound having 2-12 carbon atoms.
[22] The method of [21], wherein (C) a diol compound having 2-12 carbon atoms is one or more compounds selected from the group consisting of hexylglycerol and cyclohexylglycerol.

Effect of the Invention

According to the present invention, propagation of not only bacterium but also mold and the like can be prevented and cosmetics superior in the preservative quality can be provided.

According to the present invention, moreover, cosmetics free of or with less peculiar odor or cosmetics imparted with a desired aroma can be provided safely.

According to the present invention, since an antiseptic effect can be exhibited in any container filled with cosmetics, refillable cosmetics can also be provided.

DESCRIPTION OF EMBODIMENTS

[(A) Acylproline]

In the present invention, acylproline is represented by the formula (I):

In the formula (I),

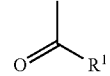

is also shown as $R^1$—CO— in the present specification.

The acyl group represented by $R^1$—CO— is an acyl group induced from a saturated or unsaturated fatty acid having 2-23 carbon atoms, namely, an acyl residue of the saturated or unsaturated fatty acid. Examples thereof include acetyl group, isopropanoyl group, propanoyl group, butanoyl group, isobutanoyl group, sec-butanoyl group, tert-butanoyl group, pentanoyl group, sec-pentanoyl group, tert-pentanoyl group, isopentanoyl group, hexanoyl group, heptanoyl group, octanoyl group, 2-ethylhexanoyl group, tert-octanoyl group, nonanoyl group, isononanoyl group, decanoyl group, isodecanoyl group, undecanoyl group, lauroyl group, undecylenoyl group, myristoyl group, palmitoyl group, stearoyl group, behenoyl group and oleoyl group.

The long chain acyl group represented by $R^1$—CO— may be an acyl group induced from a single composition acid, or an acyl group induced from naturally obtained mixed fatty acid such as coconut oil fatty acid, castor oil fatty acid, olive oil fatty acid, palm oil fatty acid and the like or synthetically obtained fatty acid (including branched fatty acid). One kind of these may be used, or two or more kinds selected from the above-mentioned group may be used in a mixture.

The acyl group represented by $R^1$—CO— is preferably an acyl group induced from saturated or unsaturated fatty acid having 4-18 carbon atoms, more preferably an acyl group induced from saturated or unsaturated fatty acid having 6-12 carbon atoms, further preferably an acyl group induced from saturated or unsaturated fatty acid having 8-10 carbon atoms, more preferably a decanoyl group.

Therefore, $R^1$ in the formula is a hydrocarbon group having 1-22 carbon atoms. Examples of the "hydrocarbon group" include chain hydrocarbon groups such as an alkyl group, an alkynyl group and the like. A chain hydrocarbon group is preferable, and both straight chain and branched chain can be used. An alkyl group is more preferable, which more preferably has 3-17, more preferably 5-11, more preferably 7-9, carbon atoms.

Examples of the salt of the compound of the formula (I) include pharmacologically acceptable salts and the like, and include alkali metal salts such as lithium salt, sodium salt, potassium salt and the like; alkaline earth metal salts such as calcium salt, magnesium salt and the like; ammonium salt; basic organic substance salt and the like. Of these, sodium salt, potassium salt and ammonium salt are preferable, sodium salt and potassium salt are more preferable, and sodium salt is further preferable, from the aspect of solubility.

The compound represented by the formula (I) may also be a hydrate or a non-hydrate, or a non-solvate or solvate.

The production method of acyl proline of the present invention is not particularly limited, and acyl proline can be easily produced by combining known methods. Specifically, acyl proline can be prepared from proline and acid chloride using the Schotten-Baumann method including simultaneous dropwise addition of acid chloride and a base such as sodium hydroxide and the like. The proline may be an L form, a D form or a mixture thereof, preferably an L form.

The content of acylproline in the cosmetic composition of the present invention is generally not less than 0.001 wt %, preferably not less than 0.01 wt %, more preferably not less than 0.05 wt %. On the other hand, from the aspects of the texture during application of the composition, it is generally not more than 5 wt %, preferably not more than 4 wt %, more preferably not more than 3 wt %, further preferably not more than 2 wt %, particularly preferably not more than 1.5 wt %, especially preferably not more than 1 wt %, most preferably not more than 0.5 wt %.

In the present specification, "antiseptic or preservative" means prevention of invasion, development and growth of microorganisms, thereby keeping decay and fermentation from occurring. Therefore, an "antiseptic effect" means an effect of suppressing the growth of fungi such as mold and the like and bacteria to prevent denaturation of cosmetics and increase the preservative quality thereof.

(B) in the present invention is at least one kind selected from the group consisting of
a compound represented by the following formula (II) or a salt thereof

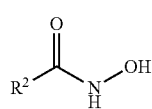
(II)

in the formula (II), $R^2$ is a hydrocarbon group having 5-11 carbon atoms or a straight chain or branched chain hydrocarbon group. For example, $R^2$ is an alkyl group having 5-11 carbon atoms, an alkenyl group having 5-11 carbon atoms, an alkynyl group having 5-11 carbon atoms or an alkoxy group having 5-11 carbon atoms, and
a compound represented by the following formula (III) or a salt thereof

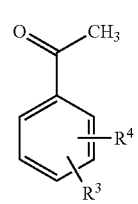
(III)

in the formula (III), $R^3$ and $R^4$ are each independently hydrogen, a hydroxy group or $—OCH_3$.

[(B-1) Hydroxamic Acid]

In the formula (II), $R^2$ is a hydrocarbon group having 5-11 carbon atoms, or a straight chain or branched chain hydrocarbon group. For example, $R^2$ is an alkyl group having 5-11 carbon atoms, an alkenyl group having 5-11 carbon atoms, an alkynyl group having 5-11 carbon atoms or an alkoxy group having 5-11 carbon atoms.

The "alkyl group having 5-11 carbon atoms" may be a straight chain or branched chain and, for example, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl and the like can be mentioned. Of these, an alkyl group having 6-10 carbon atoms is preferable, and an alkyl group having 8 carbon atoms is more preferable.

The "alkenyl group having 5-11 carbon atoms" may be a straight chain or branched chain and, for example, 1-pentenyl, 2-pentenyl, 3-pentenyl, 4-pentenyl, 1-hexenyl, 2-hexenyl, 3-hexenyl, 5-hexenyl, 1-heptenyl, 1-octenyl, 1-nonenyl, 1-decenyl, 1-undecenyl and the like can be mentioned. Of these, an alkenyl group having 6-10 carbon atoms is preferable, and an alkenyl group having 8 carbon atoms is more preferable.

The "alkynyl group having 5-11 carbon atoms" may be straight chain or branched chain, for example, 1-pentynyl, 2-pentynyl, 3-pentynyl, 4-pentynyl, 4-methyl-3-pentynyl, 1-hexynyl, 3-hexynyl, 5-hexynyl, 1-heptynyl, 1-octynyl, 1-nonynyl, 1-decynyl, 1-undecynyl and the like can be mentioned. Of these, an alkynyl group having 6-10 carbon atoms is preferable, and an alkynyl group having 8 carbon atoms is more preferable.

Examples of the "alkoxy group having 5-11 carbon atoms" include pentyloxy, hexyloxy, heptyloxy, octyloxy, nonyloxy, decyloxy, and undecyloxy. Of these, an alkoxy group having 6-10 carbon atoms is preferable, and an alkoxy group having 8 carbon atoms is more preferable.

As a compound represented by the formula (II), octanohydroxamic acid, heptanohydroxamic acid, or hexanohydroxamic acid is preferable, and octanohydroxamic acid is more preferable.

Examples of the salt of the compound of the formula (II) include pharmacologically acceptable salts and the like, and include alkali metal salts such as lithium salt, sodium salt, potassium salt and the like; alkaline earth metal salts such as calcium salt, magnesium salt and the like; ammonium salt; basic organic substance salt and the like. Of these, sodium salt, potassium salt and ammonium salt are preferable, sodium salt and potassium salt are more preferable, and sodium salt is further preferable, from the aspect of broad utility.

The compound represented by the formula (II) may also be a hydrate or a non-hydrate, or a non-solvate or solvate.

The compound represented by the formula (II) or a salt thereof to be used may be any of one obtained by a chemical synthesis method, a natural one derived from animal or plant, and one obtained by a fermentation method or gene recombination method. For example, it can be synthesized by reacting the corresponding alkylhydroxylamine with an active carbonyl compound such as active ester, acid chloride and the like.

The content of the compound represented by the formula (II) in the cosmetic composition of the present invention is generally not less than 0.001 wt %, preferably not less than 0.005 wt %, more preferably not less than 0.01 wt %, from the aspects of antiseptic effect. It is generally not more than 1 wt %, preferably not more than 0.5 wt %, more preferably not more than 0.1 wt %.

[(B-2) Acetophenone Derivative]

In the formula (III), $R^3$ and $R^4$ are each independently hydrogen, a hydroxy group or —$OCH_3$.

Of the compounds represented by the formula (III), (III-a) acetophenone

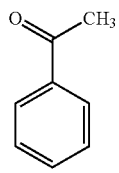

(III-b) 2-hydroxyacetophenone

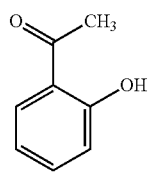

(III-c) 3-hydroxyacetophenone

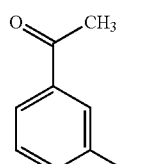

(III-d) 4-hydroxyacetophenone

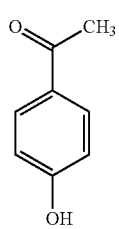

or a mixture of the above-mentioned compounds is preferable. Particularly, (III-a) acetophenone and (III-d) 4-hydroxyacetophenone are more preferable.

Examples of the salt of the compound of the formula (I) include pharmacologically acceptable salts and the like, and include alkali metal salts such as lithium salt, sodium salt, potassium salt and the like; alkaline earth metal salts such as calcium salt, magnesium salt and the like; ammonium salt; basic organic substance salt and the like. Of these, sodium salt, potassium salt and ammonium salt are preferable, sodium salt and potassium salt are more preferable, and sodium salt is further preferable, from the aspect of broad utility.

The compound represented by the formula (III) may also be a hydrate or a non-hydrate, or a non-solvate or solvate.

The compound represented by the formula (III) or a salt thereof to be used may be any of one obtained by a chemical synthesis method, a natural one derived from animal or plant, and one obtained by a fermentation method or gene recombination method.

The content of the compound represented by the formula (III) in the cosmetic composition of the present invention is generally not less than 0.005 wt %, preferably not less than 0.01 wt %, more preferably not less than 0.05 wt %. From the aspects of texture, stability and peculiar odor of the composition, it is generally not more than 5 wt %, preferably not more than 2 wt %, more preferably not more than 1 wt %.

From the aspects of the antiseptic effect of the composition, the content of (B-1) is generally 0.001-50 parts by weight, preferably 0.005-20 parts by weight, more preferably 0.01-5 parts by weight, per 1 part by weight of (A).

From the aspects of the antiseptic effect of the composition, the content of (B-2) is generally 0.005-50 parts by weight, preferably 0.01-20 parts by weight, more preferably 0.05-10 parts by weight, per 1 part by weight of (A).

By a combined use of the above-mentioned (A) and (B), with (C) a diol compound having 2-12 carbon atoms, the antiseptic effect can be further enhanced, and cosmetics superior in the stability and sense of use of the cosmetics can be provided.

(C) Diol Compound Having 2-12 Carbon Atoms

In the present invention, a diol compound having 2-12 carbon atoms refers to a compound having a structure wherein two carbon atoms of a chain or cyclic aliphatic hydrocarbon having 2-12 carbon atoms are each substituted by one hydroxy group. As a diol compound having 2-12 carbon atoms, a 1,2-diol compound, a 1,3-diol compound, a 1,4-diol compound, a 1,5-diol compound, a 1,6-diol compound; dipropyleneglycol and the like can be mentioned. Of these, a 1,2-diol compound, a 1,3-diol compound and dipropyleneglycol are preferable.

Specifically, 1,2-pentanediol, 3-methyl-1,3-butanediol, 2-methyl-1,3-propanediol, 1,4-butanediol, 2,4-hexanediol, 1,2-hexanediol, 1,3-butyleneglycol, 1,2-propanediol, 1,3-propanediol, caprylylglycol, glyceryl monocaprate, glyceryl monocaprylate, dipropyleneglycol and the like can be mentioned, 1,2-propanediol, 1,3-propanediol, glyceryl monocaprylate, 1,3-butyleneglycol, caprylylglycol, dipropyleneglycol, 1,2-pentanediol, and 1,2-hexanediol are preferable.

Alternatively, 1,2-pentanediol, 3-methyl-1,3-butanediol, 2-methyl-1,3-propanediol, 1,4-butanediol, 2,4-hexanediol, 1,2-hexanediol, 1,3-butyleneglycol, 1,2-propanediol, 1,3-propanediol, caprylylglycol, glyceryl monocaprate, glyceryl monocaprylate, dipropyleneglycol, decylene glycol and the like can be mentioned, and 1,2-propanediol, 1,3-propanediol, glyceryl monocaprylate, 1,3-butyleneglycol, caprylylglycol, dipropyleneglycol, 1,2-pentanediol, 1,2-hexanediol, and decylene glycol are preferable.

In addition, hexylglycerol and cyclohexylglycerol can be mentioned as a preferable diol compound.

Hexylglycerol and cyclohexylglycerol may be any of a commercially available product, one obtained by a chemical synthesis method, a natural one derived from animal or plant, and one obtained by a fermentation method or gene recombination method.

The content of hexylglycerol or cyclohexylglycerol or a mixture thereof in the cosmetic composition of the present invention is generally not less than 0.01 wt %, preferably not less than 0.05 wt %, more preferably not less than 0.09 wt %. From the aspects of texture, and stability of the composition, it is generally not more than 4 wt %, preferably not more than 2 wt %, more preferably not more than 1.5 wt %. When hexylglycerol and cyclohexylglycerol are used in combination, the total amount only needs to fall within the above-mentioned range. While the weight ratio for combined use is not particularly limited, hexylglycerol:cyclohexylglycerol is generally 1:99-20:1, preferably 1:40-10:1.

From the aspects of sense of use and influence on the formulation, the content of (C) in the composition of the present invention is generally not less than 0.01 wt %, preferably not less than 0.05 wt %, more preferably not less than 0.1 wt %. It is generally not more than 15 wt %, preferably not more than 10 wt %, more preferably not more than 8 wt %.

From the aspects of the antiseptic effect, the content of (C) is generally 0.01-500 parts by weight, preferably 0.1-100 parts by weight, more preferably 0.2-20 parts by weight, per 1 part by weight of (A).

Preferably, from the aspects of the antiseptic effect, the content of (A) is 0.001-5 parts by weight, the content of (B-1) is 0.001-1 wt % and/or the content of (B-2) is 0.005-5 wt %, and the content of (C) is 0.01-15 wt %, in 100 wt % of the cosmetic composition of the present invention.

More preferably, from the similar aspects, the content of (A) is 0.05-2 parts by weight, the content of (B-1) is 0.01-0.1 wt % and/or the content of (B-2) is 0.05-1 wt %, and the content of (C) is 0.1-8 wt %, in 100 wt % of the cosmetic composition of the present invention.

Preferably, from the similar aspects, the content of (A) is 0.001-5 parts by weight, the content of (B-1) is 0.001-1 wt % and/or the content of (B-2) is 0.005-5 wt %, and the content of hexylglycerol and/or cyclohexylglycerol is 0.01-4 wt %, in 100 wt % of the cosmetic composition of the present invention.

An embodiment of a cosmetic composition comprising the above-mentioned (A) and (C) and a diol compound having 2-12 carbon atoms is also encompassed in the present invention.

As (C) a diol compound having 2-12 carbon atoms, hexylglycerol and cyclohexylglycerol are preferable.

Also, (C) a diol compound having 2-12 carbon atoms may be a combination of at least one compound selected from the group consisting of hexylglycerol and cyclohexylglycerol, and a diol compound having 2-12 carbon atoms other than hexylglycerol and cyclohexylglycerol (abbreviated as other compound (C)).

Examples of other compound (C) include the compounds described in the above-mentioned (C), and preferred are, for example, 1,2-pentanediol, 3-methyl-1,3-butanediol, 1,2-hexanediol, 1,3-butyleneglycol, 1,2-propanediol, 1,3-propanediol, caprylylglycol, glyceryl monocaprate, glyceryl monocaprylate, dipropyleneglycol and the like.

Specific examples of other compound (C) include 1,2-pentanediol, 3-methyl-1,3-butanediol, 2-methyl-1,3-propanediol, 1,4-butanediol, 2,4-hexanediol, 1,2-hexanediol, 1,3-butyleneglycol, 1,2-propanediol, 1,3-propanediol, caprylylglycol, glyceryl monocaprate, glyceryl monocaprylate, dipropyleneglycol, decylene glycol and the like, and 1,2-propanediol, 1,3-propanediol, glyceryl monocaprylate, 1,3-butyleneglycol, caprylylglycol, dipropyleneglycol, 1,2-pentanediol, 1,2-hexanediol, and decylene glycol are preferable.

The content of hexylglycerol or cyclohexylglycerol or a mixture thereof in the composition of the present invention is generally not less than 0.01 wt %, preferably not less than 0.05 wt %, more preferably not less than 0.09 wt %. From the aspects of texture and stability of the composition, it is generally not more than 4 wt %, preferably not more than 2 wt %, more preferably not more than 1.5 wt %.

From the aspects of the antiseptic effect of the composition, the content of hexylglycerol and/or cyclohexylglycerol is generally 0.01-50 parts by weight, preferably 0.05-20 parts by weight, more preferably 0.1-10 parts by weight, per 1 part by weight of (A).

From the aspects of the antiseptic effect of the composition, the content of other compound (C) is generally 0.01-500 parts by weight, preferably 0.1-100 parts by weight, more preferably 0.2-20 parts by weight, per 1 part by weight of (A).

Preferably, from the similar aspects, the content of (A) is 0.001-5 parts by weight and the content of hexylglycerol and/or cyclohexylglycerol is 0.01-4 wt %, in 100 wt % of the cosmetic composition of the present invention.

More preferably, from the similar aspects, the content of (A) is 0.001-5 parts by weight, the content of hexylglycerol and/or cyclohexylglycerol is 0.09-1.5 wt %, and the content of other compound (C) is 0.05-8 wt %, in 100 wt % of the cosmetic composition of the present invention.

The pH of the composition of the present invention is preferably not less than 3.0, more preferably not less than 4.0, particularly preferably not less than 4.5, from the aspects of suppression of damage on the skin and hair, stability of formulation, and foaming in the case of cleaning agents. In addition, the pH is preferably not more than 10.0, more preferably not more than 8.0, particularly preferably not more than 7.5.

The form of the cosmetic composition of the present invention is not particularly limited, and may take any form such as liquid, emulsion, paste, gel, solid, powder and the like. Of these, liquid, emulsion, paste or gel is preferable.

Examples of the cosmetic composition of the present invention include skin cosmetics such as facial cleanser, skin lotion, skin milk, cream, gel, serum, facial mask, mask, soap, body shampoo, face powder, foundation, lip rouge, blush, eyeliner, mascara, eye shadow, eyebrow pencil and the like, and hair cosmetics such as shampoo, rinse, conditioner, hair styling agent, hair treatment and the like. While the cosmetic composition can be formulated into any cosmetic, skin cosmetics such as facial cleanser, skin lotion, skin milk, cream, gel, serum, facial mask, mask, body shampoo and the like, or hair cosmetics such as shampoo, rinse, conditioner, hair treatment and the like are preferable. A skin cosmetic required to provide moisturizing is more preferable.

While the cosmetic composition of the present invention can be used as it is as a cosmetic, or may contain a component that can be generally added to cosmetic agents as long as the effect of the present invention is not inhibited. Specific examples thereof include oil solutions, chelating agents, surfactants, powders, amino acids, polyamino acids and a salt thereof, sugar alcohol and alkylene oxide adducts thereof, lower alcohols, animal and plant extracts, nucleic acids, vitamins, enzymes, anti-inflammatory agents, antimicrobial agents, preservatives, antioxidants, moisturizer, thickener, viscosity modifier, UV absorbers, adiaphoretics, pigments, dyes, flavors, pH adjusters, pearly sheen agents, wetting agents and the like. These are mere examples and components other than these can be added.

Examples of the oil solution include fatty acids such as isostearic acid, undecylenoic acid, oleic acid and the like; esters such as myristyl myristate, hexyl laurate, decyl oleate, isopropyl myristate, hexyldecyl dimethyl octanoate, glycerine monostearate, diethyl phthalate, ethylene glycol monostearate, cetyl octanoate, octyl oxystearate, benzoic acid alkyl ester and the like; hydrocarbons such as liquid paraffin, polyisobutene, petrolatum, squalane and the like; wax such as lanolin, reduced lanolin, carnauba wax and the like; fats and oils such as silicone oil, mink oil, cacao oil, coconut oil, palm kernel oil, camellia oil, sesame oil, castor oil, olive oil, jojoba oil and the like; cooligomers of ethylene and α-olefin, and the like.

A particular example of the silicone oil is silicone oil selected from ether-modified silicone such as methylpolysiloxane, polymeric methylpolysiloxane, polyoxyethylene/methylpolysiloxane copolymer, polyoxypropylene/methylpolysiloxane copolymer and poly(oxyethylene, oxypropylene)/methylpolysiloxane copolymer and the like, stearoxymethylpolysiloxane, stearoxytrimethylsilane, methylhydrogen polysiloxane, cyclic silicone such as decamethylcyclopentasiloxane, octamethylcyclotetrasiloxane, tetrahydrotetramethylcyclotetrasiloxane, methylcyclopolysiloxane, dodecamethylcyclohexasiloxane and the like; methylphenylpolysiloxane, trimethylsiloxysilicate, amino-modified silicone such as aminoethylaminopropylsiloxane/dimethylsiloxane copolymer and the like, silanol-modified polysiloxane, alkoxy-modified polysiloxane, fatty acid-modified polysiloxane, fluorine-modified polysiloxane, epoxy-modified polysiloxane, alkoxy-modified polysiloxane perfluoropolyether, polyvinyl acetate dimethyl polysiloxane, and mixtures thereof.

While the chelating agent is not particularly limited, preferable examples thereof include a chelating agent selected from triethylenetetramine, 2-thenoyltrifluoroacetone, thioglycolic acid, tartaric acid, succinic acid, 8-quinolinol, pyridine-2,6-dicarboxylic acid, pyridine, 1,10-phenanthroline, lactic acid, 8-hydroxyquinoline-5-sulfonic acid, glycine, 2,2'-pyridylethylenediamine, aurintricarboxylic acid, xylenol orange, 5-sulfosalicylic acid, salicylic acid, pyrocatechol-3,5-disulfonate, 4,5-dihydroxybenzene-1,3-disulfonic acid, 1,2-diaminocyclohexane-N,N,N',N'-tetraacetic acid, citric acid, oxalate, nitrilotriacetic acid, ethylenediamine-N,N,N',N'-tetraacetic acid (EDTA), acetylacetone and a salt thereof, and mixtures thereof and the like.

Examples of the surfactant include anionic surfactants such as N-long chain acylamino acid salt (N-long chain acyl acidic amino acid salt, N-long chain acyl neutral amino acid salt and the like), N-long chain fatty acid acyl-N-methyl taurate, alkyl sulfate and an alkylene oxide adduct thereof, fatty acid amide ether sulfate, metal salt and weak base salt of fatty acid, sulfosuccinate surfactant, alkylphosphate and an alkylene oxide adduct thereof, alkyl ether carboxylic acid and the like; non-ionic surfactants such as ether-type surfactant (glycerine ether and an alkylene oxide adduct thereof and the like), ester-type surfactant (glycerine ester and an alkylene oxide adduct thereof and the like), ether ester-type surfactant (sorbitan ester and an alkylene oxide adduct thereof and the like), ester-type surfactant (polyoxyalkylene fatty acid ester, glycerine ester, fatty acid polyglycerine ester, sorbitan ester, sucrose fatty acid ester and the like), alkylglucosides, hydrogenated castor oil pyroglutamic acid diester and an ethylene oxide adduct thereof, nitrogen-containing non-ionic surfactants (fatty acid alkanolamide and the like), cationic surfactants such as aliphatic amine salt (alkylammonium chloride, dialkylammonium chloride and the like), quaternary ammonium salt thereof, aromatic quaternary ammonium salt (a benzalkonium salt and the like), fatty acid acyl arginine ester and the like; amphoteric surfactant such as betaine-type surfactant (carboxybetaine and the like), aminocarboxylic acid-type surfactant, imidazoline-type surfactant and the like, and the like.

Examples of the powder include resin powder such as nylon beads, silicone beads and the like, nylon powder, metal fatty acid soap, yellow iron oxide, red iron oxide, black iron oxide, chromium oxide, cobalt oxide, carbon black, ultramarine, iron blue, zinc oxide, titanium oxide, zirconium oxide, silicon oxide, aluminum oxide, cerium oxide, titanated mica, boron nitride, barium sulfate, calcium carbonate, magnesium carbonate, aluminum silicate, magnesium silicate, silicon carbide, dye, lake, sericite, mica, talc, kaolin, plate-shaped barium sulfate, butterfly-shaped barium sulfate, fine particles of titanium oxide, fine particles of zinc oxide, fine particles of iron oxide, acyl amino acid such as acyl lysine, acylglutamic acid, acylarginine, acylglycine and the like and the like. Furthermore, surface treatment such as silicone treatment, fluorine compound treatment, silane coupling agent treatment, silane treatment, organic titanate treatment, acylated lysine treatment, fatty acid treatment, metallic soap treatment, oil solution treatment, amino acid treatment and the like may be applied.

Examples of the amino acid include glycine, alanine, serine, threonine, arginine, glutamic acid, aspartic acid, isoleucine, leucine, valine and the like.

Examples of the polyamino acid and a salt thereof include polyglutamic acid, polyaspartic acid and the like.

Examples of the sugar alcohol and an alkylene oxide adduct thereof include mannitol, sorbitol and the like.

Examples of the lower alcohol include ethanol, propanol and the like.

Examples of the animal and plant extracts include lecithin, gelatin and the like; examples of the nucleic acid include disodium 5'-inosinate, disodium 5'-uridylate and the like; examples of the vitamins include vitamin A, C etc. and a derivative thereof and the like; examples of the enzyme include papain, protease and the like; examples of the anti-inflammatory agent include potassium glycyrrhizinate and the like; examples of the antimicrobial agent include triclosan, trichloro calban, octopirox, zinc pyrithione and the like; examples of the preservative include methylparaben, butylparaben and the like; examples of the antioxidant include dibutylhydroxytoluene and the like; examples of the moisturizer include isopentyldiol, Luvitol and the like; examples of the thickener include hydroxypropyl starch phosphoric acid and the like; examples of the viscosity modifier include polyoxyalkylenesorbitan ester, polyoxyethyleneglycol distearate, ethanol and the like; examples of the UV absorber include octyl methoxycinnamate and the like; examples of the adiaphoretic include aluminum oxide and the like; examples of the pigment include titanium dioxide and the like; examples of the dye include tar dye, inorganic dye, dye derived from natural-base and the like; flavor; examples of the pH adjuster include citric acid, trisodium citrate, sodium carbonate, phosphoric acid and the like; examples of the pearly sheen agent include ethyleneglycol distearate and the like; and examples of the wetting agent include propyleneglycol and the like.

The production method of the cosmetic composition of the present invention is not particularly limited, and the cosmetic composition can be produced by a conventional method by selecting and adding essential components (A) and (B), further (C), and various components generally necessary for producing a cosmetic composition (the above-mentioned other components, water etc.) as appropriate.

A method of preserving cosmetics comprising a step of adding the above-mentioned (A) and (B) to cosmetics is also the second embodiment of the present invention. The order of addition of (A) and (B) may be any and either one may be added first or both of them may be added simultaneously. The method may further comprise a step of adding (C). The definition of each is as mentioned above. For example, the method includes a step of adding 0.001-5 wt % of (A), 0.001-1 wt % of (B-1) and/or 0.005-5 wt % of (B-2), and 0.01-15 wt % of (C) to cosmetics.

Alternatively, the method includes a step of adding 0.001-5 wt % of (A), 0.001-1 wt % of (B-1) and/or 0.005-5 wt % of (B-2), and 0.01-4 wt % of hexylglycerol and/or cyclohexylglycerol to cosmetics.

A preservative containing the above-mentioned (A) and (B) is also another embodiment of the present invention. For example, the content of (B-1) is 0.001-50 parts by weight, preferably 0.005-20 parts by weight, more preferably 0.01-5 parts by weight, per 1 part by weight of (A).

Similarly, the content of (B-2) in the preservative is generally 0.005-50 parts by weight, preferably 0.01-20 parts by weight, more preferably 0.05-10 parts by weight, per 1 part by weight of (A).

The preservative may further contain (C). The content of (C) in the preservative is generally 0.01-500 parts by weight, preferably 0.1-100 parts by weight, more preferably 0.2-20 parts by weight, per 1 part by weight of (A).

Similarly, the content of hexylglycerol and/or cyclohexylglycerol in the preservative is generally 0.01-50 parts by weight, preferably 0.05-20 parts by weight, more preferably 0.1-10 parts by weight, per 1 part by weight of (A).

A method of preserving cosmetics comprising a step of adding the above-mentioned (A) and (C) to cosmetics is also another embodiment of the present invention. The order of addition of (A) and (C) may be any and either one may be added first or both of them may be added simultaneously. As (C), hexylglycerol and/or cyclohexylglycerol are/is preferable. Each definition is as described above. For example, the method includes a step of adding 0.001-5 wt % of (A) and 0.01-4 wt % of hexylglycerol and/or cyclohexylglycerol to cosmetics.

A method of preserving cosmetics comprising a step of adding 0.001-5 wt % of (A), 0.01-4 wt % of hexylglycerol and/or cyclohexylglycerol and 0.01-15 wt % of other compound (C) to cosmetics is also encompassed in the embodiment of the present invention.

A preservative comprising the above-mentioned (A) and (C) is also another embodiment of the present invention. For example, the content of hexylglycerol and/or cyclohexylglycerol is 0.01-50 parts by weight, preferably 0.05-20 parts by weight, more preferably 0.1-10 parts by weight, per 1 part by weight of (A).

The preservative may further contain other compound (C). The content of (C) in the preservative is generally 0.01-500 parts by weight, preferably 0.1-100 parts by weight, more preferably 0.2-20 parts by weight, per 1 part by weight of (A). Each definition is as described above.

The present invention is explained in more detail in the following by referring to Examples, which are not to be construed as limitative.

EXAMPLES

<Synthetic Example 1> Synthesis of Decanoylproline

Proline (manufactured by Ajinomoto Co., Inc.) (34.54 g) was dissolved in water (100 g), decanoyl chloride (manufactured by Tokyo Chemical Industry Co., Ltd.) (52.01 g) and 25% aqueous sodium hydroxide solution were added while adjusting to pH 12. The mixture was neutralized with 75% sulfuric acid, the aqueous layer was removed, water and ethyl acetate were added, and the aqueous layer was removed. Ethyl acetate was evaporated under reduced pressure to give decanoylproline (68.12 g).

<Synthetic Example 2> Preparation of Decanoyl Prolinate Sodium Salt

Decanoylproline obtained in Synthetic Example 1 was suspended in a suitable amount of water and neutralized to pH 5 with sodium hydroxide to give a decanoyl prolinate sodium salt.

<Experimental Example 1> Antiseptic Property Evaluation of Skin Lotion Formulation Preparation of Skin Lotion Formulation The formulation was prepared based on a known method. That is, each component shown in Table 1 except citric acid was stirred until uniformity while heating at 70° C., and the mixture was cooled to near room temperature, adjusted to pH 5.5 with citric acid and finally adjusted with the amount of water to 100%.

Antiseptic Property Test

A preservative effectiveness test was performed based on "the Japanese Pharmacopoeia, supplement of the 14th edition, 5. preservatives effectiveness test".

1. Test Strains
E.c; *Escherichia coli* NBRC 3972
P.a; *Pseudomonas aeruginosa* NBRC 13275
S.a; *Staphylococcus aureus* NBRC 13276
C.a; *Candida albicans* NBRC 1594
A.b; *Aspergillus brasiliensis* NBRC 9455

2. Preparation of Test Microorganism Culture
(1) Bacterium
Microorganisms precultivated in SCD agar medium at 30° C. for 20 hr were scraped with a platinum loop, suspended in sterile saline, and adjusted to about $10^8$ cells/mL to give a test microorganism culture.
(2) Yeast
Microorganisms precultivated in potato dextrose agar medium at 25° C. for 48 hr were scraped with a platinum loop, suspended in sterile saline, and adjusted to about $10^8$ cells/mL to give a test microorganism culture.
(3) Mold
Microorganisms precultivated in potato dextrose agar medium at 25° C. for 7 days were scraped with a platinum loop, suspended in 0.05% polysorbate 80-added sterile saline, and adjusted to about $10^7$ cells/mL to give a test microorganism culture.

3. Inoculation and Preservation of Microorganisms
A sample (20 g) per one kind of a test microorganism was placed in a sterile vial container, and 0.2 mL of the test microorganism culture was inoculated. Each was preserved at 25° C., and viable counts were measured on day 7, 14, 21, 28.

4. Interpretation
Using the following medium, the viable counts were measured by a pour method.
bacterium: SCDLP agar medium
fungi: GPLP agar medium
The evaluation was performed according to the following m interpretation criteria 1.
(Interpretation Criteria 1)
Bacterium and *Candida*
⊙: Viable counts decrease to less than 10 in the test period on day 7 after inoculation, and stay in that level until completion of 28 day test period.
x: failure to meet criteria of ⊙
*Aspergillus brasiliensis*
⊙: Viable counts thereof decrease to not more than 0.1% of the inoculum counts by day 7 after inoculation, and stay at a level equal to or not more than that until completion of 28 day test period.
○: Viable counts thereof decrease to not more than 1% of the inoculum counts by day 7 after inoculation, and stay at a level equal to or not more than that until completion of 28 day test period.
Δ: Viable counts thereof decrease to not more than 10% of the inoculum counts by day 7 after inoculation, and stay at a level equal to or not more than that until completion of 28 day test period.
x: failure to meet criteria of Δ.

TABLE 1

Table 1 Antiseptic property evaluation of skin lotion formulation

| | | Ex. 1 | Comp. Ex. 1 | Comp. Ex. 2 | Comp. Ex. 3 | Comp. Ex. 4 | Comp. Ex. 5 | Ex. 2 | Comp. Ex. 6 | Comp. Ex. 7 | Comp. Ex. 8 |
|---|---|---|---|---|---|---|---|---|---|---|---|
| | hyaluronic acid Na | 0.10 | 0.10 | 0.10 | 0.10 | 0.10 | 0.10 | 0.10 | 0.10 | 0.10 | 0.10 |
| | sorbitol | 5.00 | 5.00 | 5.00 | 5.00 | 5.00 | 5.00 | 5.00 | 5.00 | 5.00 | 5.00 |
| | PCA-Na | 1.50 | 1.50 | 1.50 | 1.50 | 1.50 | 1.50 | 1.50 | 1.50 | 1.50 | 1.50 |
| | glycerol | 5.00 | 5.00 | 5.00 | 5.00 | 5.00 | 5.00 | 5.00 | 5.00 | 5.00 | 5.00 |
| component (A) | decanoylproline Na | 0.50 | — | 0.50 | 2.00 | — | — | 0.50 | — | — | 2.00 |
| component (B) | capurylhydroxamic acid | 0.08 | — | — | — | 0.08 | 0.12 | 0.04 | 0.04 | 0.08 | — |
| component (C) | propanediol | — | — | — | — | — | — | — | 0.46 | 0.46 | 0.92 | 0.46 |
| | citric acid Na citric acid | 0.20 to pH 5.5 | 0.20 to pH 5.5 | 0.20 to pH 5.5 | 0.20 to pH 5.5 | 0.20 to pH 5.5 | 0.20 to pH 5.5 | 0.20 to pH 5.5 | 0.20 to pH 5.5 | 0.20 to pH 5.5 | 0.20 to pH 5.5 |
| | water | balance | balance | balance | balance | balance | balance | balance | balance | balance | balance |
| | total | 100.00 | 100.00 | 100.00 | 100.00 | 100.00 | 100.00 | 100.00 | 100.00 | 100.00 | 100.00 |
| results | | | | | | | | | | | |
| | E.c (*Escherichia coli*) | ⊙ | X | ⊙ | ⊙ | X | X | ⊙ | X | X | ⊙ |
| | P.a (*Pseudomonas aeruginosa*) | ⊙ | X | X | X | ⊙ | ⊙ | ⊙ | ⊙ | ⊙ | X |
| | S.a (*Staphylococcus aureus*) | ⊙ | X | ⊙ | ⊙ | X | X | ⊙ | X | X | ⊙ |
| | C.a (*Candida albicans*) | ⊙ | X | ⊙ | ⊙ | X | X | ⊙ | X | ⊙ | ⊙ |
| | A.b (*Aspergillus brasiliensis*) | ⊙ | X | Δ | ○ | Δ | ○ | ⊙ | X | Δ | Δ |

Formulations of Examples 1 and 2 were confirmed to have an antimicrobial action on bacterium, *Candida* and *Aspergillus brasiliensis*.

<Experimental Example 2> Antiseptic Property Evaluation of Liquid Cleansing Formulation Preparation of Liquid Wash Formulation The formulation was prepared based on a known method. That is, each component shown in Table 2 except NaOH was stirred until uniformity while heating at 70° C., and the mixture was cooled to near room temperature, adjusted to pH 5.4 with NaOH and finally adjusted with the amount of water to 100%.

Antiseptic Property Test

Interpreted by the same method as in Experimental Example 1 and using interpretation criteria 1. Table 2 shows the results of *Aspergillus brasiliensis*. They were interpreted as ⊙ for all three kinds of the aforementioned bacterium and *Candida*. Formulations of Examples 3 and 4 were confirmed to have an antimicrobial action on bacterium and *Aspergillus brasiliensis*.

TABLE 2

Table 2 Antifungal evaluation of liquid cleansing formulation

| | | Ex. 3 | Ex. 4 | Comp. Ex. 9 | Comp. Ex. 10 | Comp. Ex. 11 | Comp. Ex. 12 | Comp. Ex. 13 | Comp. Ex. 14 | Comp. Ex. 15 |
|---|---|---|---|---|---|---|---|---|---|---|
| | water | 43.700 | 43.700 | 43.700 | 43.700 | 43.700 | 43.700 | 43.700 | 43.700 | 43.700 |
| | cocoylglutamic acid 2Na, cocoylglutamic acid Na (total 25%) | 10.000 | 10.000 | 10.000 | 10.000 | 10.000 | 10.000 | 10.000 | 10.000 | 10.000 |
| | cocoglucoside (52%) | 6.000 | 6.000 | 6.000 | 6.000 | 6.000 | 6.000 | 6.000 | 6.000 | 6.000 |
| | arginine | 0.300 | 0.300 | 0.300 | 0.300 | 0.300 | 0.300 | 0.300 | 0.300 | 0.300 |
| | water | 25.000 | 25.000 | 25.000 | 25.000 | 25.000 | 25.000 | 25.000 | 25.000 | 25.000 |
| component (A) | decanoylproline Na | 1.000 | 1.000 | — | 1.000 | 2.000 | — | — | — | 1.000 |
| component (B) | caprylhydroxamic acid | 0.016 | 0.016 | — | — | — | 0.016 | 0.016 | 0.080 | — |
| component (C) | propanediol | — | 0.184 | — | — | — | — | 0.184 | 0.920 | 0.184 |
| component (C) | glyceryl caprylate | 2.000 | 2.000 | 2.000 | 2.000 | 2.000 | 2.000 | 2.000 | 2.000 | 2.000 |
| | 20% aqueous citric acid solution | 3.000 | 3.000 | 3.000 | 3.000 | 3.000 | 3.000 | 3.000 | 3.000 | 3.000 |

TABLE 2-continued

Table 2 Antifungal evaluation of liquid cleansing formulation

|  | Ex. 3 | Ex. 4 | Comp. Ex. 9 | Comp. Ex. 10 | Comp. Ex. 11 | Comp. Ex. 12 | Comp. Ex. 13 | Comp. Ex. 14 | Comp. Ex. 15 |
|---|---|---|---|---|---|---|---|---|---|
| 3% NaOH water | pH 5.4 balance | pH 5.4 balance | pH 5.4 balance | pH 5.4 balance | pH 5.4 balance | pH 5.4 balance | pH 5.4 balance | pH 5.4 balance | pH 5.4 balance |
| total results | 100.000 | 100.000 | 100.000 | 100.000 | 100.000 | 100.000 | 100.000 | 100.000 | 100.000 |
| A.b (*Aspergillus brasiliensis*) | ○ | ○ | X | Δ | Δ | Δ | Δ | Δ | Δ |

<Experimental Example 3> Antiseptic Property Evaluation of Cream Formulation

Preparation of Cream Formulation

Preparations of Examples 5-7, Comparative Examples 16-25

The components of (I) described in Table 3 and Table 4 were dissolved by stirring with heating and components (II), (A), (B), after preliminary mixing with heating, were added to allow for emulsification. The mixture was allowed to cool by stirring, and adjusted to pH 5.5 or pH 6.8 with 3% aqueous sodium hydroxide or citric acid solution. The prepared compositions were preserved at room temperature.

Antiseptic Property Test

The antiseptic property was evaluated according to the interpretation criteria 1. The results are shown in Table 3. Formulations of Examples 5 and 6 were confirmed to have an antimicrobial action on bacterium, *Candida* and *Aspergillus brasiliensis*. According to the sensory evaluation, a peculiar odor was confirmed with cream containing not less than 0.3% of hydroxyacetophenone; however, the peculiar odor was suppressed and was not felt when combined with decanoylproline.

TABLE 3

Antiseptic property evaluation of cream formulation

| | | Ex. 5 | Ex. 6 | Comp. Ex. 16 | Comp. Ex. 17 | Comp. Ex. 18 | Comp. Ex. 19 | Comp. Ex. 20 | Comp. Ex. 21 | Comp. Ex. 22 | Comp. Ex. 23 |
|---|---|---|---|---|---|---|---|---|---|---|---|
| component (A) | decanoylproline Na | 0.5 | 0.5 | — | 0.5 | 2.0 | 0.5 | — | — | — | — |
| component (B) | hydroxyacetophenone | 0.3 | 0.3 | — | — | — | — | 0.3 | 0.5 | 0.3 | 0.5 |
| I | squalane | 5.0 | 5.0 | 5.0 | 5.0 | 5.0 | 5.0 | 5.0 | 5.0 | 5.0 | 5.0 |
| | jojoba oil | 5.0 | 5.0 | 5.0 | 5.0 | 5.0 | 5.0 | 5.0 | 5.0 | 5.0 | 5.0 |
| | *macadamia* nut oil | 5.0 | 5.0 | 5.0 | 5.0 | 5.0 | 5.0 | 5.0 | 5.0 | 5.0 | 5.0 |
| | tri(capric acid/caprylic acid)glyceryl | 5.0 | 5.0 | 5.0 | 5.0 | 5.0 | 5.0 | 5.0 | 5.0 | 5.0 | 5.0 |
| | lauroylglutamic acid di(phytosteryl/octyldodecyl) | 1.0 | 1.0 | 1.0 | 1.0 | 1.0 | 1.0 | 1.0 | 1.0 | 1.0 | 1.0 |
| | isostearyl hydroxystearate | 2.0 | 2.0 | 2.0 | 2.0 | 2.0 | 2.0 | 2.0 | 2.0 | 2.0 | 2.0 |
| | shea butter | 2.0 | 2.0 | 2.0 | 2.0 | 2.0 | 2.0 | 2.0 | 2.0 | 2.0 | 2.0 |
| | stearyl alcohol | 3.8 | 3.8 | 3.8 | 3.8 | 3.8 | 3.8 | 3.8 | 3.8 | 3.8 | 3.8 |
| | Carnauba wax | 0.1 | 0.1 | 0.1 | 0.1 | 0.1 | 0.1 | 0.1 | 0.1 | 0.1 | 0.1 |
| | glyceryl stearate | 2.9 | 2.9 | 2.9 | 2.9 | 2.9 | 2.9 | 2.9 | 2.9 | 2.9 | 2.9 |
| II | xanthan gum | 0.2 | 0.2 | 0.2 | 0.2 | 0.2 | 0.2 | 0.2 | 0.2 | 0.2 | 0.2 |
| | water | balance | balance | balance | balance | balance | balance | balance | balance | balance | balance |
| | sucrose palmitate | 0.4 | 0.4 | 0.4 | 0.4 | 0.4 | 0.4 | 0.4 | 0.4 | 0.4 | 0.4 |
| | stearoylglutamic acid Na | 0.2 | 0.2 | 0.2 | 0.2 | 0.2 | 0.2 | 0.2 | 0.2 | 0.2 | 0.2 |
| | citric acid Na | 0.2 | 0.2 | 0.2 | 0.2 | 0.2 | 0.2 | 0.2 | 0.2 | 0.2 | 0.2 |
| | citric acid or aqueous sodium hydroxide solution | to pH 5.5 | to pH 6.8 | to pH 5.5 | to pH 5.5 | to pH 5.5 | to pH 6.8 | to pH 5.5 | to pH 5.5 | to pH 6.8 | to pH 6.8 |
| | total (%) results | 100.00 | 100.00 | 100.00 | 100.00 | 100.00 | 100.00 | 100.00 | 100.00 | 100.00 | 100.00 |
| | E.c (*Escherichia coli*) | ⊙ | ⊙ | X | ⊙ | ⊙ | ⊙ | X | X | X | X |
| | P.a (*Pseudomonas aeruginosa*) | ⊙ | ⊙ | X | X | X | X | ⊙ | ⊙ | ⊙ | ⊙ |
| | S.a (*Staphylococcus aureus*) | ⊙ | ⊙ | X | ⊙ | ⊙ | ⊙ | X | X | X | X |
| | C.a (*Candida albicans*) | ⊙ | ⊙ | X | X | ⊙ | X | X | X | X | X |

TABLE 3-continued

| Antiseptic property evaluation of cream formulation | | | | | | | | | | |
|---|---|---|---|---|---|---|---|---|---|---|
| | Ex. 5 | Ex. 6 | Comp. Ex. 16 | Comp. Ex. 17 | Comp. Ex. 18 | Comp. Ex. 19 | Comp. Ex. 20 | Comp. Ex. 21 | Comp. Ex. 22 | Comp. Ex. 23 |
| A.b (*Aspergillus brasiliensis*) | ⊙ | ⊙ | X | Δ | ◯ | Δ | X | ⊙ | X | ⊙ |

*Aspergillus brasiliensis* was interpreted according to the interpretation criteria 1. The results are shown in Table 4. Example 7 was confirmed to have an extremely superior antimicrobial action. According to the sensory evaluation, a peculiar odor was confirmed with cream containing 0.2% of hydroxyacetophenone; however, the peculiar odor was suppressed when combined with decanoylproline.

TABLE 4

| Antiseptic property evaluation of cream formulation | | | | |
|---|---|---|---|---|
| | | Ex. 7 | Comp. Ex. 24 | Comp. Ex. 25 |
| component (A) | decanoylproline Na | 0.5 | — | — |
| component (B) | acetophenone | 0.2 | 0.2 | 0.5 |
| I | squalane | 5.0 | 5.0 | 5.0 |
| | jojoba oil | 5.0 | 5.0 | 5.0 |
| | *macadamia* nut oil | 5.0 | 5.0 | 5.0 |
| | tri(capric acid/caprylic acid)glyceryl | 5.0 | 5.0 | 5.0 |
| | lauroylglutamic acid di(phytosteryl/octyldodecyl) | 1.0 | 1.0 | 1.0 |
| | isostearyl hydroxystearate | 2.0 | 2.0 | 2.0 |
| | shea butter | 2.0 | 2.0 | 2.0 |
| | stearyl alcohol | 3.8 | 3.8 | 3.8 |
| | Carnauba wax | 0.1 | 0.1 | 0.1 |
| | glyceryl stearate | 2.9 | 2.9 | 2.9 |
| II | xanthan gum | 0.2 | 0.2 | 0.2 |
| | water | balance | balance | balance |
| | sucrose palmitate | 0.4 | 0.4 | 0.4 |
| | stearoylglutamic acid Na | 0.2 | 0.2 | 0.2 |
| | citric acid Na | 0.2 | 0.2 | 0.2 |
| | citric acid or aqueous sodium hydroxide solution | to pH 5.5 | to pH 5.5 | to pH 5.5 |
| | total (%) | 100.00 | 100.00 | 100.00 |
| results | | | | |
| | A.b (*Aspergillus brasiliensis*) | ⊙ | X | X |

<Experimental Example 4> Antiseptic Property Evaluation of Skin Lotion Formulation Preparation of Examples 8-19, Comparative Examples 26-32

The components of (I) described in Table 5 were dissolved by stirring with heating and components (II) after heating was added and the mixture was cooled to near room temperature. Then, the components of (III) preliminarily dissolved by stirring, and the components of (A)-(C) were added, and the mixture was dissolved by stirring and adjusted to pH 5.0 or pH 6.5. The prepared composition was preserved at room temperature.
Evaluation: Antiseptic Effect (Mold)
(1) A microorganism culture of *Aspergillus brasiliensis* (A.b) was added to each composition (1 mL), prepared as mentioned above, at an initial microorganism number of $10^5$ cells per 1 mL.
(2) The formulation of (1) was preserved at 25° C. for 3 days.
(3) After 3 days, the formulation (10 μL) and the following medium (190 μL) were mixed well on a 96 well plate, preserved at 25° C. for 18 hr, and the degree of mold growth was evaluated by visual observation and according to the following criteria. medium composition: GPLP medium "DAIGO" (Wako Pure Chemical Industries, Ltd.) 3.71 g, lecithin: Wako primary 0.43 g, polysorbate 80: Wako for biochemical 2.90 g, ion exchange water 260 g
Evaluation Criteria of Degree of Mold Growth:
0: no growth of mold
1: slight growth
2: growth, less than ⅓ of well
3: growth, not less than ⅓ of well
4: during propagation, well is generally covered with microorganisms
The experiment was repeated 3 times, and average values of 3 evaluations were determined as the growth condition score of A.b.
(Interpretation Criteria 2)
⊙: A.b growth condition score less than 1.0
◯: A.b growth condition score not less than 1.0 and less than 1.5
Δ: A.b growth condition score not less than 1.5 and less than 2.5
x: A.b growth condition score not less than 2.5

TABLE 5

| Antiseptic property evaluation of skin lotion formulation | | | | | | | | | | | |
|---|---|---|---|---|---|---|---|---|---|---|---|
| | | Ex. 8 | Ex. 9 | Ex. 10 | Ex. 11 | Ex. 12 | Ex. 13 | Ex. 14 | Ex. 15 | Ex. 16 | Ex. 17 |
| component (A) | decanoylproline Na | 1.00 | 1.00 | 1.00 | 1.00 | 0.50 | 0.30 | 1.00 | 1.00 | 0.30 | 0.30 |
| component (B) | 4-hydroxy-acetophenone | 0.20 | 0.20 | 0.15 | 0.15 | 0.20 | 0.30 | — | — | 0.15 | 0.15 |
| | acetophenone | — | — | — | — | — | — | 0.20 | 0.10 | — | — |
| | caprylhydroxamic acid | — | — | — | — | — | — | — | — | 0.01 | 0.01 |
| component (C) | DPG | 2.00 | 2.00 | 2.00 | 2.00 | 2.00 | 2.00 | 2.00 | 2.00 | 2.00 | 2.00 |
| | BG | 3.00 | 3.00 | 3.00 | 3.00 | 3.00 | 3.00 | 3.00 | 3.00 | 3.00 | 3.00 |
| | caprylylglycol | — | — | — | — | — | — | — | — | — | — |
| | NaOH aqueous solution | pH 5.0 | pH 6.5 | pH 5.0 | pH 6.5 | pH 5.0 | pH 5.0 | pH 5.0 | pH 5.0 | pH 5.0 | pH 6.5 |

TABLE 5-continued

Antiseptic property evaluation of skin lotion formulation

| | | | | | | | | | | | |
|---|---|---|---|---|---|---|---|---|---|---|---|
| I | lauroylglutamic acid di(phytosteryl/octyldodecyl) | 0.35 | 0.35 | 0.35 | 0.35 | 0.35 | 0.35 | 0.35 | 0.35 | 0.35 | 0.35 |
| | cetyl octanoate | 0.15 | 0.15 | 0.15 | 0.15 | 0.15 | 0.15 | 0.15 | 0.15 | 0.15 | 0.15 |
| | PPG-8 ceteth 20 | 0.50 | 0.50 | 0.50 | 0.50 | 0.50 | 0.50 | 0.50 | 0.50 | 0.50 | 0.50 |
| | PPG-6 decyltetra deceth-30 | 0.50 | 0.50 | 0.50 | 0.50 | 0.50 | 0.50 | 0.50 | 0.50 | 0.50 | 0.50 |
| | glycerol | 1.25 | 1.25 | 1.25 | 1.25 | 1.25 | 1.25 | 1.25 | 1.25 | 1.25 | 1.25 |
| II | water | 5.00 | 5.00 | 5.00 | 5.00 | 5.00 | 5.00 | 5.00 | 5.00 | 5.00 | 5.00 |
| III | water | 75.00 | 75.00 | 75.00 | 75.00 | 75.00 | 75.00 | 75.00 | 75.00 | 75.00 | 75.00 |
| | citric acid | 0.20 | 0.20 | 0.20 | 0.20 | 0.20 | 0.20 | 0.20 | 0.20 | 0.20 | 0.20 |
| | water | balance | balance | balance | balance | balance | balance | balance | balance | balance | balance |
| | total (%) | 100.00 | 100.00 | 100.00 | 100.00 | 100.00 | 100.00 | 100.00 | 100.00 | 100.00 | 100.00 |
| | antiseptic effect (mold) | ⊙ | ⊙ | ○ | ○ | ○ | ⊙ | ⊙ | ⊙ | ⊙ | ⊙ |

| | | Ex. 18 | Ex. 19 | Comp. Ex. 26 | Comp. Ex. 27 | Comp. Ex. 28 | Comp. Ex. 29 | Comp. Ex. 30 | Comp. Ex. 31 | Comp. Ex. 32 |
|---|---|---|---|---|---|---|---|---|---|---|
| component (A) | decanoylproline Na | 0.30 | 1.00 | 1.00 | 2.00 | — | — | — | — | — |
| component (B) | 4-hydroxyacetophenone | — | 0.25 | — | — | 0.2 | 0.3 | — | 0.15 | — |
| | acetophenone | — | — | — | — | — | — | 0.2 | — | — |
| | caprylhydroxamic acid | 0.01 | — | — | — | — | — | — | 0.01 | 0.01 |
| component (C) | DPG | 2.00 | — | 2.00 | 2.00 | 2.00 | 2.00 | 2.00 | 2.00 | 2.00 |
| | BG | 3.00 | — | 3.00 | 3.00 | 3.00 | 3.00 | 3.00 | 3.00 | 3.00 |
| | caprylylglycol | 0.2 | — | — | — | — | — | — | — | 0.2 |
| | NaOH aqueous solution | pH 5.0 | pH 5.0 | pH 5.0 | pH 5.0 | pH 5.0 | pH 5.0 | pH 5.0 | pH 5.0 | pH 5.0 |
| I | lauroylglutamic acid di(phytosteryl/octyldodecyl) | 0.35 | 0.35 | 0.35 | 0.35 | 0.35 | 0.35 | 0.35 | 0.35 | 0.35 |
| | ocetyl octanoate | 0.15 | 0.15 | 0.15 | 0.15 | 0.15 | 0.15 | 0.15 | 0.15 | 0.15 |
| | PPG-8 ceteth 20 | 0.50 | 0.50 | 0.50 | 0.50 | 0.50 | 0.50 | 0.50 | 0.50 | 0.50 |
| | PPG-6 decyltetra deceth-30 | 0.50 | 0.50 | 0.50 | 0.50 | 0.50 | 0.50 | 0.50 | 0.50 | 0.50 |
| | glycerol | 1.25 | 1.25 | 1.25 | 1.25 | 1.25 | 1.25 | 1.25 | 1.25 | 1.25 |
| II | water | 5.00 | 5.00 | 5.00 | 5.00 | 5.00 | 5.00 | 5.00 | 5.00 | 5.00 |
| III | water | 75.00 | 75.00 | 75.00 | 75.00 | 75.00 | 75.00 | 75.00 | 75.00 | 75.00 |
| | citric acid | 0.20 | 0.20 | 0.20 | 0.20 | 0.20 | 0.20 | 0.20 | 0.20 | 0.20 |
| | water | balance | balance | balance | balance | balance | balance | balance | balance | balance |
| | total (%) | 100.00 | 100.00 | 100.00 | 100.00 | 100.00 | 100.00 | 100.00 | 100.00 | 100.00 |
| | antiseptic effect (mold) | ⊙ | ⊙ | X | X | Δ | Δ | X | Δ | X |

Evaluation by interpretation criteria 2 is shown in Table 5. The formulations of Examples 8-19 showed a superior antiseptic effect against mold. In addition, a peculiar odor was confirmed with the 4-hydroxyacetophenone and acetophenone-containing skin lotion of Comparative Examples 28-31, but a peculiar odor was suppressed in Examples 8-19.

<Experimental Example 5> Antiseptic Property Evaluation of Skin Lotion Formulation Preparation of Skin Lotion Formulation The formulation was prepared based on a known method. That is, each component shown in Table 6 except citric acid was stirred until uniformity while heating at 70° C., and the mixture was cooled to near room temperature, adjusted to pH 5.0 with aqueous sodium hydroxide solution and finally adjusted with the amount of water to 100%. The antiseptic effect was evaluated by a method similar to that in Experimental Example 4.

The evaluation according to interpretation criteria 2 is shown in Table 6. The formulations of Examples 20-27 showed a superior antiseptic effect against mold.

TABLE 6

Antiseptic property evaluation of skin lotion formulation

| | | Ex. 20 | Ex. 21 | Comp. Ex. 33 | Comp. Ex. 34 | Ex. 22 | Comp. Ex. 35 | Ex. 23 | Ex. 24 | Comp. Ex. 36 | Comp. Ex. 37 |
|---|---|---|---|---|---|---|---|---|---|---|---|
| component (A) | decanoylproline Na | 0.20 | 0.30 | — | 0.60 | 0.30 | — | 0.50 | 0.50 | — | — |
| component (B) | 4-hydroxyacetophenone | | | — | — | 0.10 | 0.15 | — | 0.10 | — | 0.10 |
| | hexylglycerol | 0.30 | 0.20 | 0.60 | | 0.10 | 0.20 | — | — | — | |
| | cyclohexylglycerol | — | — | — | — | — | | 0.90 | 0.30 | 1.50 | 0.60 |
| component (C) | DPG | 2.00 | 2.00 | 2.00 | 2.00 | 2.00 | 2.00 | 2.00 | 2.00 | 2.00 | |
| | BG | 3.00 | 3.00 | 3.00 | 3.00 | 3.00 | 3.00 | 3.00 | 3.00 | 3.00 | |
| | caprylylglycol | — | — | — | — | — | — | — | — | — | — |
| | 1,2-hexanediol | — | — | — | — | — | — | — | — | — | — |
| | ethylhexylglycerol | — | — | — | — | — | — | — | — | — | — |
| | NaOH aqueous solution | pH 5.0 | pH 5.0 | pH 5.0 | pH 5.0 | pH 5.0 | pH 5.0 | pH 5.0 | pH 5.0 | pH 5.0 | pH 5.0 |
| I | lauroylglutamic acid di(phytosteryl/octyldodecyl) | 0.35 | 0.35 | 0.35 | 0.35 | 0.35 | 0.35 | 0.35 | 0.35 | 0.35 | 0.35 |
| | cetyl octanoate | 0.15 | 0.15 | 0.15 | 0.15 | 0.15 | 0.15 | 0.15 | 0.15 | 0.15 | 0.15 |
| | PPG-8 ceteth 20 | 0.50 | 0.50 | 0.50 | 0.50 | 0.50 | 0.50 | 0.50 | 0.50 | 0.50 | 0.50 |
| | PPG-6 decyltetradeceth-30 | 0.50 | 0.50 | 0.50 | 0.50 | 0.50 | 0.50 | 0.50 | 0.50 | 0.50 | 0.50 |
| | glycerol | 1.25 | 1.25 | 1.25 | 1.25 | 1.25 | 1.25 | 1.25 | 1.25 | 1.25 | 1.25 |
| II | water | 5.00 | 5.00 | 5.00 | 5.00 | 5.00 | 5.00 | 5.00 | 5.00 | 5.00 | 5.00 |
| III | water | 75.00 | 75.00 | 75.00 | 75.00 | 75.00 | 75.00 | 75.00 | 75.00 | 75.00 | 75.00 |
| | citric acid | 0.20 | 0.20 | 0.20 | 0.20 | 0.20 | 0.20 | 0.20 | 0.20 | 0.20 | 0.20 |
| | water | balance | balance | balance | balance | balance | balance | balance | balance | balance | balance |
| | | 100.00 | 100.00 | 100.00 | 100.00 | 100.00 | 100.00 | 100.00 | 100.00 | 100.00 | 100.00 |
| | antiseptic effect (mold) | ⊙ | ⊙ | Δ | X | ⊙ | X | ⊙ | ⊙ | X | Δ |

| | | Comp. Ex. 38 | Ex. 25 | Comp. Ex. 39 | Ex. 26 | Comp. Ex. 40 | Comp. Ex. 41 | Ex. 27 | Comp. Ex. 42 | Comp. Ex. 43 |
|---|---|---|---|---|---|---|---|---|---|---|
| component (A) | decanoylproline Na | — | 0.50 | — | — | 0.30 | — | 0.20 | — | — |
| component (B) | 4-hydroxyacetophenone | 0.10 | 0.10 | — | 0.15 | 0.18 | 0.30 | 0.30 | 0.30 | 0.30 |
| | hexylglycerol | — | — | — | — | — | — | — | — | — |
| | cyclohexylglycerol | 0.30 | — | — | — | — | — | — | — | — |
| component (C) | DPG | | 2.00 | 2.00 | 2.00 | 2.00 | 2.00 | 2.00 | 2.00 | 2.00 |
| | BG | | 3.00 | 3.00 | 3.00 | 3.30 | 4.00 | 3.00 | 3.00 | 3.00 |
| | caprylylglycol | — | 0.10 | 0.60 | 0.20 | 0.10 | 0.60 | — | — | — |
| | 1,2-hexanediol | — | — | — | — | — | — | — | 0.30 | — |
| | ethylhexylglycerol | — | — | — | — | — | — | — | — | 0.20 |
| | NaOH aqueous solution | pH 5.0 | pH 5.0 | pH 5.0 | pH 5.0 | pH 5.0 | pH 5.0 | pH 5.0 | pH 5.0 | pH 5.0 |
| I | lauroylglutamic acid di(phytosteryl/octyldodecyl) | 0.35 | 0.35 | 0.35 | 0.35 | 0.35 | 0.35 | 0.35 | 0.35 | 0.35 |
| | cetyl octanoate | 0.15 | 0.15 | 0.15 | 0.15 | 0.15 | 0.15 | 0.15 | 0.15 | 0.15 |
| | PPG-8 ceteth 20 | 0.50 | 0.50 | 0.50 | 0.50 | 0.50 | 0.50 | 0.50 | 0.50 | 0.50 |
| | PPG-6 decyltetradeceth-30 | 0.50 | 0.50 | 0.50 | 0.50 | 0.50 | 0.50 | 0.50 | 0.50 | 0.50 |
| | glycerol | 1.25 | 1.25 | 1.25 | 1.25 | 1.25 | 1.25 | 1.25 | 1.25 | 1.25 |

TABLE 6-continued

Antiseptic property evaluation of skin lotion formulation

| | | | | | | | | | | |
|---|---|---|---|---|---|---|---|---|---|---|
| II | water | 5.00 | 5.00 | 5.00 | 5.00 | 5.00 | 5.00 | 5.00 | 5.00 | 5.00 |
| III | water | 75.00 | 75.00 | 75.00 | 75.00 | 75.00 | 75.00 | 75.00 | 75.00 | 75.00 |
| | citric acid | 0.20 | 0.20 | 0.20 | 0.20 | 0.20 | 0.20 | 0.20 | 0.20 | 0.20 |
| | water | balance | balance | balance | balance | balance | balance | balance | balance | balance |
| | | 100.00 | 100.00 | 100.00 | 100.00 | 100.00 | 100.00 | 100.00 | 100.00 | 100.00 |
| | antiseptic effect (mold) | X | ⊙ | Δ | Δ | ○ | Δ | ⊙ | Δ | Δ |

<Experimental Example 6> Antiseptic Property Evaluation of Cream Formulation

Preparation of Cream Formulation

The components of (I) described in Table 7 were dissolved by stirring with heating and components (II), (A), (B), after preliminary mixing with heating, were added to allow for emulsification. The mixture was allowed to cool by stirring, and adjusted to pH 5.5 or pH 6.8 with 3% aqueous sodium hydroxide or citric acid solution. The prepared compositions were preserved at room temperature.

Antiseptic Property Test

The antiseptic property was evaluated according to interpretation criteria 1. The results are shown in Table 7. The formulations of Examples 28 and 29 were confirmed to have an antimicrobial action on bacterium and *Aspergillus brasiliensis*.

TABLE 7

Antiseptic property evaluation of cream formulation

| | | Ex. 28 | Ex. 29 | Comp. Ex. 44 |
|---|---|---|---|---|
| component (A) | decanoylproline Na | 0.5 | 0.5 | — |
| component (B) | 4-hydroxyacetophenone | 0.1 | 0.1 | 0.2 |
| component (C) | caprylylglycol | 0.2 | 0.2 | 0.2 |
| I | squalane | 5.0 | 5.0 | 5.0 |
| | jojoba oil | 5.0 | 5.0 | 5.0 |
| | *macadamia* nut oil | 5.0 | 5.0 | 5.0 |
| | tri(capric acid/caprylic acid) glyceryl | 5.0 | 5.0 | 5.0 |
| | lauroylglutamic acid di(phytosteryl/octyldodecyl) | 1.0 | 1.0 | 1.0 |
| | isostearyl hydroxystearate | 2.0 | 2.0 | 2.0 |
| | shea butter | 2.0 | 2.0 | 2.0 |
| | stearyl alcohol | 3.8 | 3.8 | 3.8 |
| | Carnauba wax | 0.1 | 0.1 | 0.1 |
| | glyceryl stearate | 2.9 | 2.9 | 2.9 |

TABLE 7-continued

Antiseptic property evaluation of cream formulation

| | | Ex. 28 | Ex. 29 | Comp. Ex. 44 |
|---|---|---|---|---|
| II | xanthan gum | 0.2 | 0.2 | 0.2 |
| | water | balance | balance | balance |
| | sucrose palmitate | 0.4 | 0.4 | 0.4 |
| | stearoylglutamic acid Na | 0.2 | 0.2 | 0.2 |
| | citric acid Na | 0.2 | 0.2 | 0.2 |
| | citric acid or aqueous sodium hydroxide solution | to pH 5.5 | to pH 6.8 | to pH 6.8 |
| | total | 100.00 | 100.00 | 100.00 |
| results | | | | |
| | E.c (*Escherichia coli*) | ⊙ | ⊙ | X |
| | P.a (*Pseudomonas aeruginosa*) | ⊙ | ⊙ | ⊙ |
| | S.a (*Staphylococcus aureus*) | ⊙ | ⊙ | X |
| | C.a (*Candida albicans*) | ⊙ | ⊙ | X |
| | A.b (*Aspergillus brasiliensis*) | ⊙ | ⊙ | ○ |

<Experimental Example 7> Antiseptic Property Evaluation of Skin Lotion Formulation Preparation of Skin Lotion Formulation The formulation was prepared based on a known method. That is, each component shown in Table 1 except citric acid was stirred until uniformity while heating at 70° C., and the mixture was cooled to near room temperature, adjusted to pH 5.5 with aqueous sodium hydroxide solution and finally adjusted with the amount of water to 100%. The antiseptic effect was evaluated by a method similar to that in Experimental Example 4.

The evaluation according to interpretation criteria 2 is shown in Table 8. The formulations of Examples 30-32 showed a superior antiseptic effect against mold.

TABLE 8

| | | Ex. 30 | Ex. 31 | Ex. 32 | Comp. Ex. 45 | Comp. Ex. 27 |
|---|---|---|---|---|---|---|
| component (A) | decanoylproline Na | 0.40 | 0.50 | 0.80 | — | 2.00 |
| component (B) | caprylhydroxamic acid | 0.048 | 0.040 | 0.016 | 0.08 | — |
| component (C) | propanediol | 0.55 | 0.46 | 0.1840 | 0.92 | — |
| | DPG | 2.00 | 2.00 | 2.00 | 2.00 | 2.00 |
| | BG | 3.00 | 3.00 | 3.00 | 3.00 | 3.00 |
| | NaOH aqueous solution | pH 5.0 | pH 5.0 | pH 5.0 | pH 5.0 | pH 5.0 |
| I | lauroylglutamic acid di(phytosteryl/octyldodecyl) | 0.35 | 0.35 | 0.35 | 0.35 | 0.35 |

TABLE 8-continued

|  |  | Ex. 30 | Ex. 31 | Ex. 32 | Comp. Ex. 45 | Comp. Ex. 27 |
|---|---|---|---|---|---|---|
|  | cetyl octanoate | 0.15 | 0.15 | 0.15 | 0.15 | 0.15 |
|  | PPG-8 ceteth 20 | 0.50 | 0.50 | 0.50 | 0.50 | 0.50 |
|  | PPG-6 decyltetra deceth-30 | 0.50 | 0.50 | 0.50 | 0.50 | 0.50 |
|  | glycerol | 1.25 | 1.25 | 1.25 | 1.25 | 1.25 |
| II | water | 5.00 | 5.00 | 5.00 | 5.00 | 5.00 |
| III | water | 75.00 | 75.00 | 75.00 | 75.00 | 75.00 |
|  | citric acid | 0.20 | 0.20 | 0.20 | 0.20 | 0.20 |
|  | water | balance | balance | balance | balance | balance |
|  |  | 100.00 | 100.00 | 100.00 | 100.00 | 100.00 |
|  | antiseptic effect (mold) | ○ | ⊙ | ⊙ | Δ | X |

The samples and reagents used are as described below.
PPG-8 ceteth 20: NIKKOLPBC-44 (manufactured by Nikko Chemicals) PPG-6 decyltetra deceth-30: NIKKOLPEN-4630 (manufactured by Nikko Chemicals)
DPG: DPG-RF (dipropyleneglycol) (manufactured by ADEKA)
BG: 1,3-BG (1,3-butyleneglycol) UK (manufactured by DAICEL)
glycerol: conc. glycerol for cosmetics (manufactured by Sakamoto Yakuhin Kogyo Co., Ltd. or manufactured by Kao Corporation)
lauroylglutamic acid di(phytosteryl/octyldodecyl): "ELDEW (Eldew)" PS-203 (manufactured by Ajinomoto Co., Inc.) cetyl octanoate: CHE (manufactured by Kokyu Alcohol Kogyo Co., Ltd.)
4-hydroxyacetophenone: 4'-hydroxyacetophenone (manufactured by Tokyo Chemical Industry Co., Ltd.)
acetophenone: acetophenone (manufactured by Tokyo Chemical Industry Co., Ltd.)
hyaluronic acid Na: Hyaluronsan HA-LQ (manufactured by QP Corporation)
sorbitol; sorbitol Kao Corporation (Kao Corporation)
PCA-Na: "AJIDEW" NL-50 (manufactured by Ajinomoto Co., Inc.) decanoylproline Na; "PRODEW" P-DS-12 (manufactured by Ajinomoto Co., Inc.)
caprylhydroxamic acid; octanohydroxamic acid (manufactured by Tokyo Chemical Industry Co., Ltd.)
glyceryl caprylate; SUNSOFT No. 700-P2 (manufactured by Taiyo chemical)
propanediol: Zemea select propanediol (manufactured by DOW) caprylhydroxamic acid, propanediol: Zeastat (manufactured by Inolex)
cocoylglutamic acid 2Na, cocoylglutamic acid Na (total 25%); "Amisoft" CS-22 (manufactured by Ajinomoto Co., Inc.)
cocoglucoside (52%): Plantacare818up (manufactured by BASF)
squalane: squalane (manufactured by Maruha)
jojoba oil: purified jojoba oil (manufactured by KOEI KOGYO Co., Ltd.)
macadamia nut oil: NIKKOL macadamia nut oil (manufactured by Nikko Chemicals)
tri(capric acid/caprylic acid)glyceryl: TCG-M (manufactured by Kokyu Alcohol Kogyo Co., Ltd.)
isostearyl hydroxystearate: SCHERCEMOL SHS Ester (manufactured by Lubrizol)
shea butter: Shea butter (manufactured by Kokyu Alcohol Kogyo Co., Ltd.)
stearyl alcohol: KALCOL 8688 (manufactured by Kao Corporation) Carnauba wax: purified Carnauba No. 1 (manufactured by CERA RICA NODA)
glyceryl stearate: NIKKOLGMS-BV2 (manufactured by Nikko Chemicals)

xanthan gum: KELTROL CG-T (manufactured by CP Kelco)
sucrose palmitate: surfhope SE COSME C-1615 (manufactured by Mitsubishi Chemical Foods)
stearoylglutamic acid Na: "Amisoft" HS-11P (manufactured by Ajinomoto Co., Inc.)
caprylylglycol: 1,2-octanediol (manufactured by Tokyo Chemical Industry Co., Ltd.)
hexylglycerol: Adekanol NHG (manufactured by ADEKA)
cyclohexylglycerol: Adekanol CHG (manufactured by ADEKA)

INDUSTRIAL APPLICABILITY

According to the present invention, a cosmetic composition having a high antiseptic effect and superior in preservative quality can be provided.

According to the present invention, moreover, since an antiseptic effect can be exhibited in any container filled with cosmetics, refillable cosmetics can also be provided safely.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

This application is based on a patent application No. 2015-112637 filed in Japan, the contents of which are is incorporated in full herein.

The invention claimed is:
1. A cosmetic composition, comprising (A) and (B):
   (A) decanoylproline or a salt thereof; and
   (B) at least one component selected from the group consisting of (a) and (b):
   (a) a compound represented by formula (II) or a salt thereof:

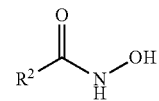

(II)

wherein R² is an alkyl group having 5 to 11 carbon atoms, an alkenyl group having 5 to 11 carbon atoms, an alkynyl group having 5 to 11 carbon atoms, or an alkoxy group having 5 to 11 carbon atoms; and
(b) a compound represented by formula (III) or a salt thereof:

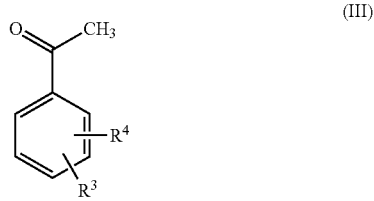

wherein R³ and R⁴ are each independently hydrogen, a hydroxy group, or —OCH₃.

2. The composition according to claim 1, wherein in (B) R² is an alkyl group having 5 to 11 carbon atoms.

3. The composition according to claim 1, wherein (B) is a compound represented by formula (II) which is octanohydroxamic acid.

4. The composition according to claim 1, wherein (B) is a compound represented by formula (III) and is

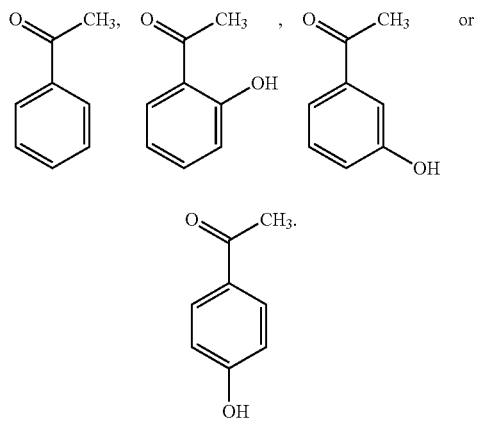

5. The composition according to claim 1, further comprising:
(C) at least one diol compound having 2 to 12 carbon atoms.

6. The composition according to claim 5, wherein (C) said at least one diol compound having 2 to 12 carbon atoms is one or more compounds selected from the group consisting of a 1,2-diol compound, a 1,3-diol compound, and dipropyleneglycol.

7. The composition according to claim 5, wherein (C) said at least one diol compound having 2 to 12 carbon atoms is one or more compounds selected from the group consisting of 1,2-pentanediol, 3-methyl-1,3-butanediol, 1,2-hexanediol, 1,3-butyleneglycol, 1,2-propanediol, 1,3-propanediol, caprylylglycol, glyceryl monocaprate, glyceryl monocaprylate, and dipropyleneglycol.

8. The composition according to claim 5, wherein (C) said at least one diol compound having 2 to 12 carbon atoms is one or more compounds selected from the group consisting of hexylglycerol and cyclohexylglycerol.

9. The composition according to claim 1, wherein (A) decanoylproline or a salt thereof is present in said composition in an amount of 0.001 to 5 wt %, based on the total weight of said composition.

10. The composition according to claim 1, wherein (B) is a compound represented by formula (II) or a salt thereof and is present in said composition in an amount of 0.001 to 1 wt %, based on the total weight of said composition.

11. The composition according to claim 1, wherein (B) is a compound represented by formula (III) or a salt thereof and is present in said composition in an amount of 0.005 to 5 wt %, based on the total weight of said composition.

12. The composition according to claim 5, wherein (C) said at least one diol compound having 2 to 12 carbon atoms is present in said composition in an amount of 0.01 to 15 wt %, based on the total weight of said composition.

13. A cosmetic composition, comprising (A), (B) and (C):
(A) decanoylproline or a salt thereof;
(B) a compound represented by formula (II) or a salt thereof;

wherein R² is an alkyl group having 5 to 11 carbon atoms, an alkenyl group having 5 to 11 carbon atoms, an alkynyl group having 5 to 11 carbon atoms, or an alkoxy group having 5 to 11 carbon atoms; and
(C) at least one diol compound having 2 to 12 carbon atoms.

14. The composition according to claim 13, wherein (C) said at least one diol compound having 2 to 12 carbon atoms is one or more compounds selected from the group consisting of hexylglycerol and cyclohexylglycerol.

15. The composition according to claim 14, wherein said one or more compounds selected from the group consisting of hexylglycerol and cyclohexylglycerol is present in said composition in an amount of 0.01 to 4 wt %, based on the total weight of said composition.

16. A method of preserving a cosmetic, comprising adding to a cosmetic the cosmetic composition according to claim 1.

17. The method according to claim 16, further comprising adding:
(C) at least one diol compound having 2 to 12 carbon atoms.

18. The method according to claim 17, wherein (C) said at least one diol compound having 2 to 12 carbon atoms is one or more compounds selected from the group consisting of hexylglycerol and cyclohexylglycerol.

19. A method of preserving a cosmetic, comprising adding to a cosmetic the cosmetic composition according to claim 13.

20. The method according to claim 19, wherein (C) said at least one diol compound having 2 to 12 carbon atoms is one or more compounds selected from the group consisting of hexylglycerol and cyclohexylglycerol.

* * * * *